United States Patent
Sevenster

(10) Patent No.: US 11,562,141 B2
(45) Date of Patent: Jan. 24, 2023

(54) MAPPING OF CODED MEDICAL VOCABULARIES

(71) Applicant: KONINKLIJKE PHILIPS N.V., Eindhoven (NL)

(72) Inventor: Merlijn Sevenster, Haarlem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 200 days.

(21) Appl. No.: 16/630,017

(22) PCT Filed: Jul. 12, 2018

(86) PCT No.: PCT/EP2018/068868
§ 371 (c)(1),
(2) Date: Jan. 10, 2020

(87) PCT Pub. No.: WO2019/016054
PCT Pub. Date: Jan. 24, 2019

(65) Prior Publication Data
US 2021/0097234 A1    Apr. 1, 2021

Related U.S. Application Data

(60) Provisional application No. 62/533,726, filed on Jul. 18, 2017.

(51) Int. Cl.
*G06F 40/12* (2020.01)
*G06F 40/279* (2020.01)
(Continued)

(52) U.S. Cl.
CPC .......... *G06F 40/274* (2020.01); *G06F 40/226* (2020.01); *G06F 40/279* (2020.01);
(Continued)

(58) Field of Classification Search
CPC ........ G06F 40/12; G06F 40/151; G06F 40/20; G06F 40/279; G06F 40/30; G16H 10/00; G16H 15/10; G16H 15/00
(Continued)

(56) References Cited

U.S. PATENT DOCUMENTS 8,589,424 B1 * 11/2013 Patel ................... G06F 16/1794
707/758
9,594,872 B2 * 3/2017 Masarie, Jr. ........... G16H 70/20
(Continued)

FOREIGN PATENT DOCUMENTS

| JP | 2007172260 A | 7/2007 |
| JP | 2007323211 A | 12/2007 |
| JP | 2009199393 A | 9/2009 |

OTHER PUBLICATIONS

International Search Report and Written Opinion dated Oct. 10, 2018 for International Application No. PCT/EP2018/068868 Filed Jul. 12, 2018.

*Primary Examiner* — Martin Lerner

(57) ABSTRACT

A system (100) includes a feature extraction engine (130), a finding code comparison engine (140), and a mapping interface (160). The feature extraction engine (130) extracts features of a statement of a finding code in a source vocabulary (110) and features of a second statement of a second finding code in a target vocabulary (112). The finding code comparison engine (140) determines a mapping between the statement of the source vocabulary and the second statement of the target vocabulary by comparing the extracted features based on at least one identified concept that comprises the extracted features. The mapping interface (160) presents the determined mapping on a display device (162).

20 Claims, 4 Drawing Sheets

(51) Int. Cl.
  *G16H 15/00* (2018.01)
  *G06F 40/274* (2020.01)
  *G06F 40/226* (2020.01)
  *G06K 9/62* (2022.01)
  *G06N 5/02* (2006.01)
(52) U.S. Cl.
  CPC ........... *G06K 9/6215* (2013.01); *G06N 5/025* (2013.01); *G16H 15/00* (2018.01)
(58) Field of Classification Search
  USPC ................ 704/1, 9, 10; 705/3; 707/749
  See application file for complete search history.

(56) References Cited

U.S. PATENT DOCUMENTS

| | | | | |
|---|---|---|---|---|
| 10,664,862 | B1* | 5/2020 | Szulczewski | G06Q 30/0251 |
| 2005/0107672 | A1* | 5/2005 | Lipscher | G16H 20/10 |
| | | | | 600/300 |
| 2008/0069448 | A1* | 3/2008 | Turner | G06F 40/284 |
| | | | | 382/176 |
| 2009/0157599 | A1* | 6/2009 | Klinkner | G06Q 30/02 |
| 2009/0248394 | A1* | 10/2009 | Sarikaya | G06F 40/44 |
| | | | | 704/4 |
| 2010/0318549 | A1* | 12/2010 | Mayr | G16H 10/60 |
| | | | | 707/759 |
| 2011/0033425 | A1* | 2/2011 | Raykov | A61P 35/02 |
| | | | | 435/235.1 |
| 2011/0288877 | A1* | 11/2011 | Ofek | G16H 50/20 |
| | | | | 707/661 |
| 2012/0110016 | A1* | 5/2012 | Phillips | G06F 16/285 |
| | | | | 707/780 |
| 2012/0296669 | A1 | 11/2012 | Hudgins | |
| 2012/0330974 | A1* | 12/2012 | Zillner | G06N 5/02 |
| | | | | 707/749 |
| 2013/0046529 | A1* | 2/2013 | Grain | G06F 40/58 |
| | | | | 704/2 |
| 2013/0144651 | A1* | 6/2013 | Rao | G06Q 10/00 |
| | | | | 705/2 |
| 2014/0067728 | A1* | 3/2014 | Ogren | G06F 40/151 |
| | | | | 706/12 |
| 2015/0106125 | A1* | 4/2015 | Farooq | G06F 40/30 |
| | | | | 705/3 |
| 2015/0149191 | A1* | 5/2015 | Lee | G06F 40/30 |
| | | | | 705/2 |
| 2016/0117445 | A1* | 4/2016 | Venkat | G16H 10/60 |
| | | | | 705/3 |
| 2016/0132648 | A1* | 5/2016 | Shah | G06F 40/274 |
| | | | | 705/2 |
| 2016/0232142 | A1* | 8/2016 | Melnikov | G06F 40/247 |
| 2016/0342746 | A1* | 11/2016 | Sarabu | G16H 70/60 |
| 2017/0235887 | A1* | 8/2017 | Cox | G06F 40/169 |
| | | | | 705/3 |
| 2017/0372442 | A1* | 12/2017 | Mejias | G16H 40/20 |
| 2018/0357381 | A1* | 12/2018 | Aldin | G06F 40/247 |
| 2019/0034407 | A1* | 1/2019 | Hagiwara | G06F 40/58 |

* cited by examiner

200

| 212 | Doppler indicates no evidence of mitral regurgitation
202 |

| Text from statement/extracted feature 204 | Polarity 210 | Identified concept 206 | Generalized concept 208 |
|---|---|---|---|
| "Mitral" | + | Mitral valve | Anatomic structure |
| "Regurgitation" | - | Regurgitation | Finding |

220

| 192 | Doppler suggests prosthetic tricuspid regurgitation which is mild
222 |

| Text from statement/extracted feature 204 | Polarity 210 | Identified concept 206 | Generalized concept 208 |
|---|---|---|---|
| "Prosthetic" | + | Prosthesis | Foreign object |
| "Tricuspid" | + | Tricuspid valve | Anatomic structure |
| "Regurgitation" | + | Regurgitation | Finding |
| "Mild" | + | Mild | Severity indicator |

FIG. 2

MAPPING OF CODED MEDICAL VOCABULARIES

CROSS REFERENCE TO RELATED APPLICATIONS

This application is the U.S. National Phase application under 35 U.S.C. § 371 of International Application No. PCT/EP2018/068868 filed Jul. 12, 2018, published as WO 2019/016054 on Jan. 24, 2019, which claims the benefit of U.S. Provisional Patent Application No. 62/533,726 filed Jul. 18, 2017. These applications are hereby incorporated by reference herein.

FIELD OF THE INVENTION

The following generally relates to medical informatics, and more specifically to mapping of vocabularies of coded medical statements between a source vocabulary and a target vocabulary.

BACKGROUND OF THE INVENTION

Coded medical vocabularies are developed by medical institutions to facilitate creating patient medical reports and/or research. A finding code is a unique alphanumeric string of a coded medical vocabulary that corresponds to an observational or a diagnostic statement. For example, in one institution's vocabulary, a finding code of "373" corresponds to the text: "The pericardium appears normal". A healthcare practitioner creates a medical report for a patient by entering one or more finding codes. The entry of finding codes, rather than the statements themselves, can be more efficient than dictating or writing statements, and can provide more consistent reporting. The corresponding statements of the entered finding codes are added to the final report or replace the finding codes in a final report. An intermediate version of the patient medical report with finding codes is often stored in a database, which can provide query access to finding codes across medical reports of a patient population.

The vocabulary of an institution includes rules that govern how finding codes are included in a report. A rule can specify that certain finding codes are mutually exclusive, e.g., finding codes A1, A2 and A3 of a vocabulary are mutually exclusive. That is, A1 cannot be included in a patient medical report with A2 or A3. Rules can include conditional logic, Boolean logic, and combinations thereof. Vocabularies are locally authored and/or locally modified. That is, local systems typically permit the entry and editing of finding codes and corresponding statements, and the local vocabularies reflect local expertise, local specialties, and/or local history. As a consequence, vocabularies can differ significantly from organization to organization.

SUMMARY OF THE INVENTION

Aspects described herein address the above-referenced problems and others.

The following describes embodiments of a system and method for mapping coded medical vocabularies. The medical vocabularies include unique finding codes and corresponding statements. The medical vocabularies can include rules that govern use of the finding codes in a coded medical report. The medical vocabularies can include statistical information about the prior use of the finding codes. Features are extracted from the corresponding statements in a source vocabulary and a target vocabulary. The extracted features are compared. Mappings are determined between the finding codes and corresponding statements of the source vocabulary and the target vocabulary based on the compared features. Computed similarity scores indicate a relative strength of individual mappings. In some embodiments, the rules are translated from the source vocabulary to the target vocabulary according to the determined mappings. In some embodiments, a user interface provides review and confirmation of the mappings. The confirmed mappings can be applied to the target vocabulary.

In one aspect, a system includes a feature extraction engine, a finding code comparison engine, and a mapping interface. The feature extraction engine extracts features of a statement of a finding code in a source vocabulary and features of a second statement of a second finding code in a target vocabulary. The finding code comparison engine determines mapping between the statement of the source vocabulary and the second statement of the target vocabulary by comparing the extracted features based on at least one identified concept that comprises the extracted features. The mapping interface presents the determined mapping on a display device.

In another aspect, a method includes extracting features of a statement of a finding code in a source vocabulary and features of a second statement of a second finding code in a target vocabulary. A mapping is determined between the statement of the source vocabulary and the second statement of the target vocabulary by comparing the extracted features based on at least one identified concept that comprises the extracted features. The determined mapping is presented on a display device.

In another aspect, a non-transitory computer-readable storage medium carrying instructions controls one or more processors to extract features of a statement of a finding code in a source vocabulary and features of a second statement of a second finding code in a target vocabulary. The one or more processors are further controlled to determine a mapping between the statement of the source vocabulary and the second statement of the target vocabulary by comparing the extracted features based on at least one identified concept that comprises the extracted features, and present the determined mapping on a display device.

These and other aspects of the invention will be apparent from and elucidated with reference to the embodiment(s) described hereinafter.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 2 illustrates examples of extracted concepts from statements.

DETAILED DESCRIPTION OF EMBODIMENTS

Figure 1:
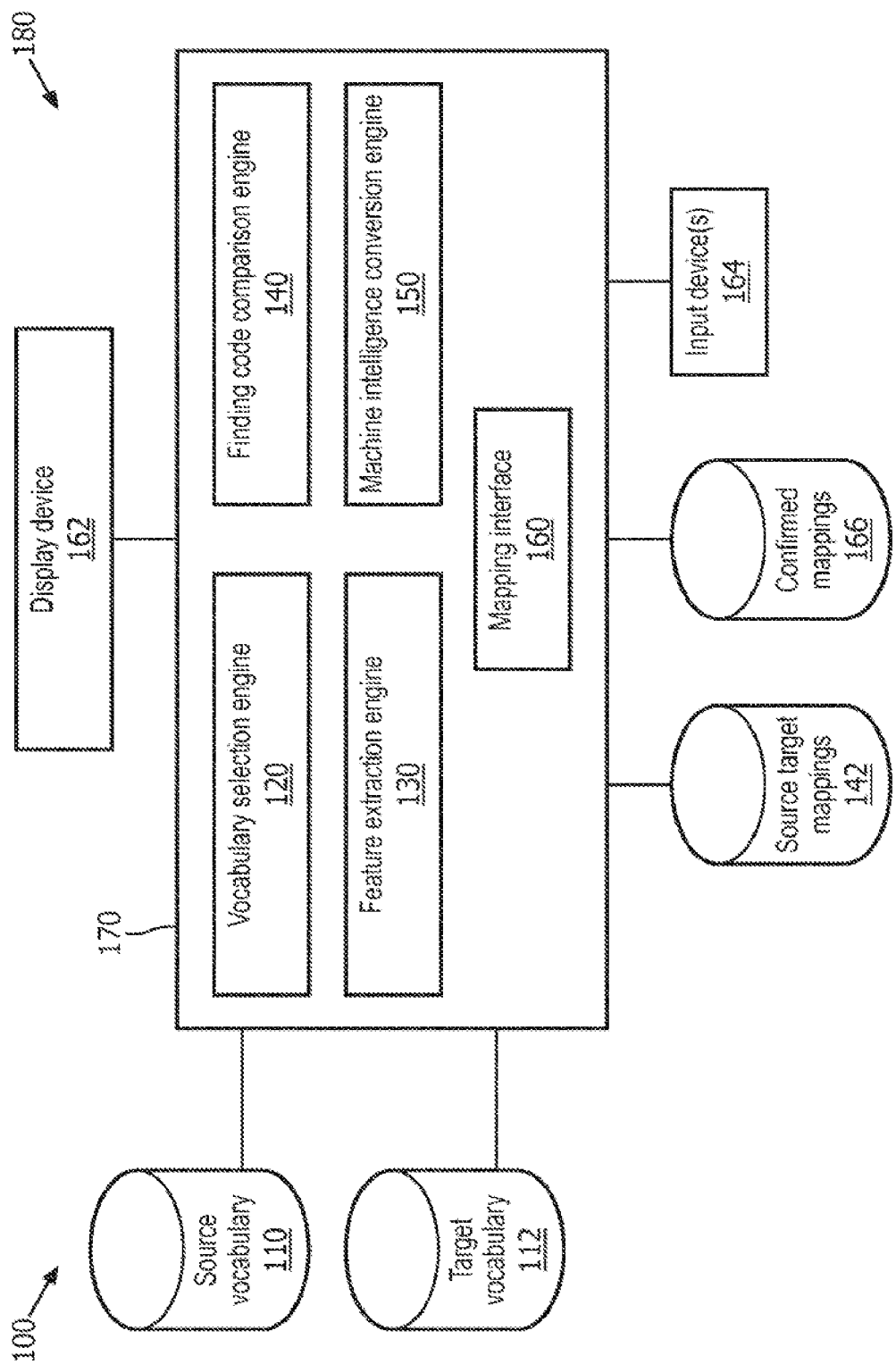
FIG. 1 schematically illustrates an embodiment of a system for mapping a source vocabulary to a target vocabulary.

With reference to FIG. 1, an embodiment of a system 100 for mapping a source vocabulary 110 to a target vocabulary 112 is schematically illustrated. Each of the vocabularies 110, 112 include unique finding codes and corresponding statements. Each of the vocabularies 110, 112 can include rules that govern a use of finding codes therein for preparing an electronic patient medical report. Each of the vocabularies 110, 112 can include statistical information about the use of the finding codes in prior electronic patient medical reports and/or other medical documents.

For example, a database stores "intermediate" reports, which are patient medical reports that include finding codes. These reports can be sampled for statistical information. The statistical information for each finding code, in one instance, includes a frequency of occurrence or relative frequency of each finding code, a distribution of time stamps of a finding code use according to the report data, and/or other statistical information. The statistical information of a finding code can be added to a record of the finding code stored in the vocabulary.

A vocabulary selection engine 120 retrieves the source vocabulary 110 and the target vocabulary 112. In some embodiments, the vocabulary selection engine 120 selects the source vocabulary 110 from a plurality of source vocabularies or a subset of the source vocabulary 110. In some embodiments, the vocabulary selection engine 120 selects the target vocabulary 112 from a plurality of target vocabularies or a subset of the target vocabulary 112. For example, some vocabularies can include subsets directed to research projects, or population-specific vocabularies, such as adult-specific vocabularies or pediatric-specific vocabularies. The vocabulary selection engine 120 can selectively retrieve the source vocabulary 110 and/or the target vocabulary 112 according to a predetermined criterion. For example, vocabularies directed to research projects can use specific ranges of finding codes, or finding codes with specific identifiers. The vocabulary selection engine 120 can select the finding codes within the specific ranges, exclude finding codes within specific ranges, select the finding codes with the specific identifiers, or exclude the finding codes with specific identifiers.

In some embodiments, the vocabulary selection engine 120 filters the source vocabulary 110 and/or the target vocabulary 112 according to the statistical information. For example, in one instance a source vocabulary is filtered to exclude finding codes below a predetermined threshold. That is, finding codes that have not been used or used very infrequently can be excluded from the vocabulary. In another example, timestamps are used to determine a current vocabulary, and frequencies of finding codes are used to determine active finding codes within the current vocabulary.

In some embodiments, the vocabulary selection engine 120 identifies corresponding rules for each finding code. The vocabulary selection engine 120 can filter finding codes according to the rules. The filtering can exclude and/or include finding codes based on the rules. For example, finding codes can be included which are not constrained by rules in a source vocabulary, such as constrained by mutual exclusion. In some instances, this can simplify processing of mappings, which are discussed in greater detail below. In another example, only those finding codes that are constrained by rules are included in the vocabulary. In some instances, this can reduce a volume of more complex mappings for another review.

A feature extraction engine 130 extracts features from the corresponding statement of each finding code in the source vocabulary 110 and the target vocabulary 112 using natural language processing (NLP) techniques. The NLP techniques include word tokenization and stemming, phrase identification, and stop word elimination. Concepts are identified from extracted words or phrases. For example, from a statement "Rocking suggests dehiscence of the aortic prosthesis," the word "suggests" is a concept of medium certainty, the word "aortic" is a concept of the aorta, the word "prosthesis" is a concept of a prosthesis, etc.

The identified concepts are generalized using an ontology, such as Systematized Nomenclature of Medicine (SNOMED), RadLex®, a locally developed ontology, combinations thereof, and the like. The generalized concepts include a foreign object, an anatomic structure, a finding, a severity indicator, a pathology, an image quality indicator, a polarity, a certainty indicator, and/or combinations thereof. Continuing the example from above, a generalized concept of certainty includes the concept of medium certainty, which includes the instance of the word "suggests." A generalized concept of an anatomic structure includes the anatomic structure of the aorta, which includes the instance of the word "aortic." A generalized concept of foreign object includes the concept of a prosthesis, which includes the instance of the word "prosthesis."

A finding code comparison engine 140 compares the extracted features to determine a mapping between statements in the source vocabulary 110 and statements in the target vocabulary 112. The finding code comparison engine 140 uses the generalized concepts to match extracted features. The comparison can include individual determinations of both present and matching, both present and not matching, both not present, and exactly one present.

Both present and matching indicates that instances of extracted features match for the same concept. For example, consider a statement of "rocking suggests dehiscence of the aortic prosthesis" from a source vocabulary, and a statement of "abnormal rocking of prosthetic aortic valve suggests dehiscence" from a target vocabulary. Present in both is the generalized concept of certainty, and the same concept of medium certainty matches with instances of the word "suggests." Present in both is the generalized concept of an anatomic structure, and the same anatomic structure of the aorta matches with instances of "aortic." Present in both is the generalized concept of a foreign object, and the concept of a prosthesis matches with instances of "prosthetic" and "prosthesis" from the same word stem.

The matching can include a word overlap ratio computed between words or phrases of the compared extracted features. The matching can be performed after the stop word elimination and/or word stemming. The ratio can be computed as a number of unique words or phrases that are in common among the extracted features of the two statements and divided by a number of unique words or phrases in either extracted feature. In some embodiments, the matching can include frequency-inverse document frequency techniques, language models, word2vec models, and combinations thereof. In some embodiments, matching can include comparison of statistical information for the finding codes. For example, a relative frequency in a population of patient medical reports can indicate a match.

Both present and not matching indicates that both the source statement and the target statement include the same generalized concept, but the concepts are different. For example, consider a statement from a source vocabulary that includes a "tricuspid valve" and a statement from a target vocabulary that includes a "mitral valve." An anatomic structure is present in both statements, but the anatomic structures do not match. That is the "tricuspid valve" and the "mitral valve" are anatomically different valves of the heart, and the "tricuspid valve" does not anatomically match the "mitral valve."

Both not present indicates that the generalized concept is not present in either of the compared statements. For example, statements may not include any foreign object. Exactly one present indicates that a single concept of one of the generalized concepts occurs in only one statement of either of the compared statements. For example, consider a first statement of "image quality is satisfactory for diagnostic interpretation" and a second statement "There is no evidence of mitral regurgitation." The concept of image quality is present in the first statement and is not present in the second statement. The concept of an anatomic structure is present in the second statement and is not present in the first statement.

The finding code comparison engine 140 computes a similarity score based on the comparison. The similarity score can be computed using rules and a point system for the individual determinations. The point system can add or subtract points from the similarity score of a mapping. For example, if a rule compares anatomical general concepts and determines that the general concept of an anatomical structure match is present in both statements and the anatomic structures match, then 5 points are added to the similarity score. In another example, if a rule compares anatomical general concepts and determines that no anatomical structure is present in either statement, then 3 points are added to the similarity score. The rules can include general comparisons of the statements. For example, points can be added for overlap of all words in the statement. An example rule multiplies the word overlap ratio by a predetermined weight.

In some embodiments, the similarity score can be computed using a statistical model or machine learning model. The statistical model can be constructed from sample data of known mappings. A known mapping is a relationship between one statement of a source vocabulary and one statement of a target vocabulary, which has been reviewed and confirmed. The machine learning model can be trained using training data of known mappings. In some embodiments, multiple similarity scores can be computed. In some embodiments, one or more of the generalized concepts can be excluded in a computed similarity score, separate similarity scores computed for different combinations of the generalized concepts, and combinations thereof. In some embodiments, the mapping can be omitted for a similarity score below a predetermined threshold value.

In some embodiments, the finding code comparison engine 140 can use prior mappings of other vocabularies. For example, if finding code A432 of source vocabulary A is mapped to B174 of target vocabulary B, when vocabulary X is being mapped to vocabulary B and the statement corresponding to finding code X662 of vocabulary X is identical to finding code of A432, the prior mapping of A432 to B174 can be used to identify a same mapping from X662 to B174. The use of prior mappings of other vocabularies can be extended to include both additional source vocabularies and/or target vocabularies. For example, if a finding code A1 maps from vocabulary A to finding code B1 of vocabulary B, X1 of vocabulary X is identical to A1, and Y1 of vocabulary Y is identical to B1, then the mapping from X1 to Y1 is the same as the mapping from A1 to B1.

The mapping can be expressed as a link between the statement from the source vocabulary 110 and the statement from the target vocabulary 112. The link can be stored in a database of source target mappings 142. The mapping can include the one or more computed similarity scores.

A machine intelligence engine 150 inputs a set of rules governing the source vocabulary 110 or source rules. The machine intelligence engine 150 identifies finding codes in the source rules and verifies mapping of the identified finding codes to the target vocabulary 112.

For all verified finding codes, the machine intelligence engine 150 converts the source rules to rules of the target vocabulary 112 or target rules. The source and/or target rules can include conditional usage. For example, a source rule specifies if finding code A1 is included then either finding code A15 or finding code A17 is additionally included. The rules can include Boolean operators. For example, a rule governs that finding code A1 is used or finding code A2 is used, but not both. With Boolean operators, exclusive OR (XOR) relationships are expressed. For example, A1 XOR A2 can be expressed with Boolean operators as (not A1 and A2) or (A1 and not A2). The rules can include combinations of conditional usage and Boolean operators.

For example, where a source rule includes A1 XOR A2 XOR A3, the machine intelligence engine 150 identifies that A1 maps to B1 of the target vocabulary, A2 maps to B2, and A3 maps to (B3 or B4), and generates a converted rule that states B1 XOR B2 XOR (B3 OR B4). The converted rule indicates that B3 and B4 can occur together or separately, but not with B1 and not with B2. B1 and B2 cannot occur together.

A mapping interface 160 controls operation of a display device 162 and one or more input devices 164 to provide review and confirmation of mapped statements between the source vocabulary 110 and the target vocabulary. Confirmed mapped statements can be stored in a confirmed mappings database 166. In some embodiments, an indicator of confirmed mappings is added to the database of source target mappings 142. The confirmed mappings can be applied to the target vocabulary 112. In some instances, the applied confirmed mappings support effective change control of the finding codes in the target vocabulary 112.

The source vocabulary 110, the target vocabulary 112, the database of source target mappings 142 and the confirmed mappings database 166 are suitably embodied by a configured electronic storage medium, such as local disk, cloud storage, server storage, remote storage and the like, accessed by a configured processor of a processing unit 170. The configured electronic storage medium can include system file structures, relational and/or object oriented database system structures, and the like.

The processing unit 170, the display device 162, and the input device(s) can comprise a computing device 180, such as a laptop computer, desktop computer, tablet computer, smartphone, body worn computing device, server, distributed or cooperative arrangement of computing devices, and the like. The display device 162 is suitably embodied by a computer display, smartphone display, projector, body worn display, television (TV), combinations thereof, and the like. The input device 164 is suitably embodied by a keyboard, a mouse, a trackball, a microphone, combinations thereof, and the like.

The vocabulary selection engine 120, the feature extraction engine 130, the finding code comparison engine 140, the machine intelligence engine 150, and the mapping interface 160 are suitably embodied by the configured computer processor, such as a digital processor, a microprocessor, an electronic processor, an optical processor, a multi-processor, a distribution of processors including peer-to-peer or cooperatively operating processors, client-server arrangement of processors, and the like and configured to select the source vocabulary 110 and the target vocabulary 112, extract features from statements of the vocabularies, identify concepts present in the statements, compare the features and concepts, determine mappings, compute similarity scores, convert source rules to target rules, review and confirm mappings, apply mappings, and operate the input device 164 and the display device 162.

The configured computer processor executes at least one computer readable instruction stored in the computer readable storage medium, such as an optical disk, a magnetic disk, semiconductor memory of a computing device with the configured processor, which excludes transitory medium and includes physical memory and/or other non-transitory medium to perform the disclosed techniques. The configured processor may also execute one or more computer readable instructions carried by a carrier wave, a signal or other transitory medium. The lines between components represented in the diagram represent communications paths.

In some embodiments, the vocabulary selection engine 120, the feature extraction engine 130, the finding code comparison engine 140, the machine intelligence conversion engine 150, and the mapping interface 160 are suitably embodied as computer program products.

With reference to FIG. 2, a first example finding code 200 and corresponding statement 202 are illustrated with extracted features 204, identified concepts 206, and generalized concepts 208. The first example statement 202 states "Doppler indicates no evidence of mitral regurgitation." The word "mitral" is included in the identified concept 206 of a mitral valve, which is included in the generalized concept 208 of an anatomical structure. The word "regurgitation" is included in the identified concept 206 of regurgitation, which is included in the generalized concept 208 of a finding.

The first example statement 202 additional includes extracted feature of "no evidence of," which is a concept of polarity 210. The concept of polarity 210 is a negation or a scope limitation applied to other concepts. The concept of polarity 210 is indicated by certain keywords, such as "no," "not," "none," and the like. The concept of polarity 210 applies a negative polarity illustrated by a "−" sign to the regurgitation.

The concept of polarity 210 can be limited by blocking keywords, such as "but." For example, consider the statement "There is no evidence of tricuspid regurgitation, but patient has rheumatic fever." The negative polarity is applied to words before the blocking keyword and is not applied to words after the blocking keyword. The scope of the polarity can include a fixed number of words.

A second example finding code 220 and corresponding statement 222 are illustrated. The second example statement 220 states "Doppler suggests prosthetic tricuspid regurgitation which is mild." The extracted text or features 204 of the second statement 222 include "prosthetic," "tricuspid," "regurgitation" and "mild." The word "prosthetic" is included within the meaning of the identified concept 206 of prosthesis, which is included in the generalized concept 208 of a foreign object. The word "tricuspid" is included within the meaning of the identified concept 206 of tricuspid valve, which is included in the generalized concept 208 of an anatomical structure. The word "regurgitation" is included within the meaning of the identified concept 206 of regurgitation, which is included in the generalized concept 208 of a finding. The word "mild" is included within the meaning of the identified concept 206 of mild, which is included in the generalized concept 208 of a severity indicator. The concept of polarity 210 can default to a positive polarity in the absence of negating words, which is illustrated in the example with a "+" sign.

The identified concept of mild can include features such as slight, minimal, nominal, and the like. In some instances, the features that comprise an identified concept include synonyms. Other examples of other identified concepts of a severity indicator can include moderate, severe, extensive, and the like. Examples of a generalized concept 208 of image quality can include aspects of image quality concepts, such as artifacts, noise, resolution, or relative quality, such as poor quality, etc. Examples of a generalized concept 208 of certainty indicators can include low, medium, high, etc.

Figure 3:
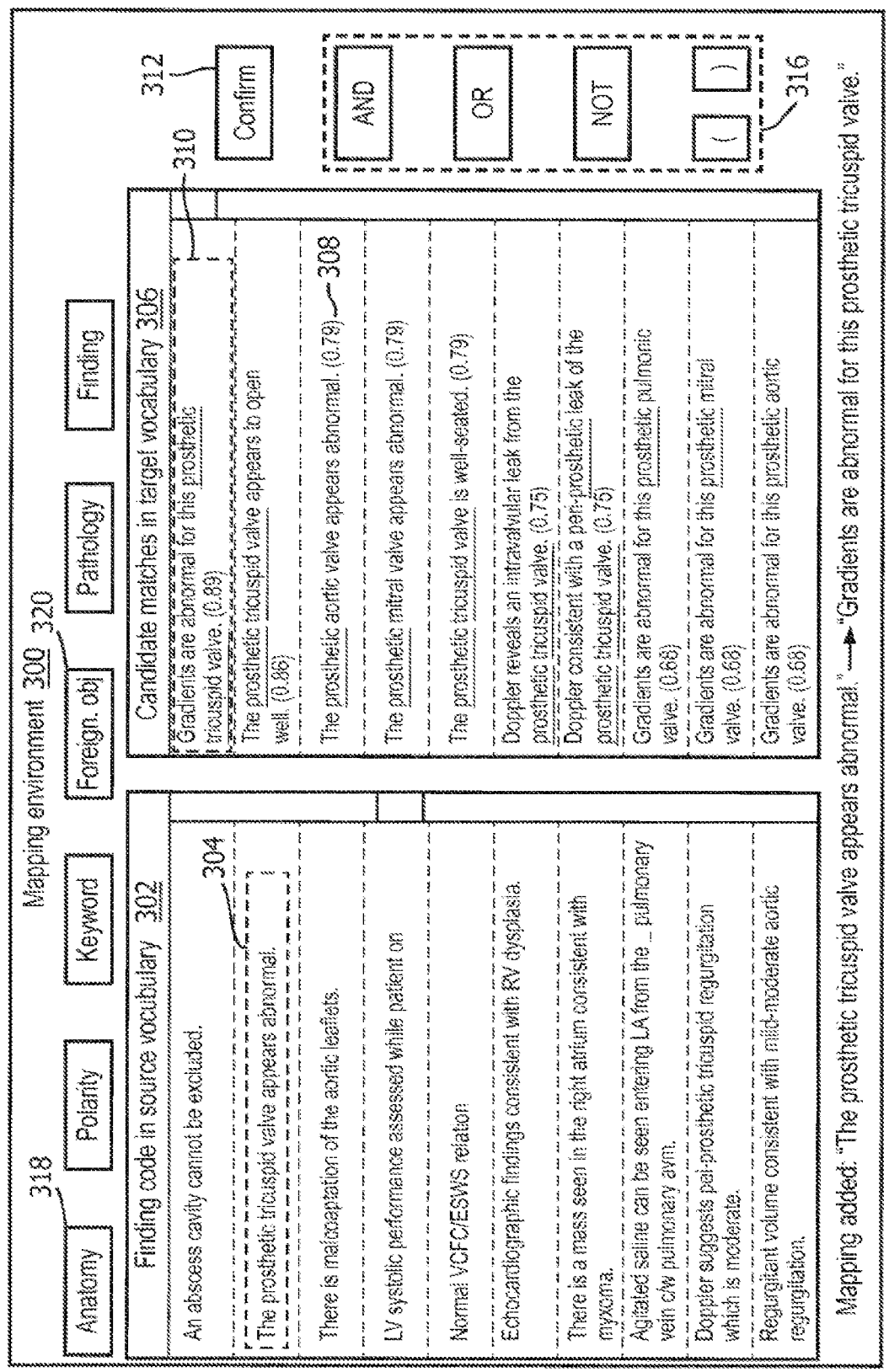
FIG. 3 illustrates an example of a display of a mapping interface for confirming a mapping between a source vocabulary and a target vocabulary.

With reference to FIG. 3 an example of a display 300 of the mapping interface 160 for confirming mappings between the source vocabulary 110 and the target vocabulary 112 is illustrated. A first region 302 lists statements of the source vocabulary 110. For example, a scrollable list includes mapped statements from the source vocabulary. The mapping interface 160 indicates a selected statement 304 from the source vocabulary 110. In the illustrated example, the selected statement 304 is indicated as selected by a dashed box. In some embodiments, the selected statement 304 can include a color change, a brightness change, and the like to indicate selection. In some embodiments, related statements according to rules can be further indicated in response to the selected statement 304. For example, statement A1 is related to statement A2 through a rule that indicates A1 XOR A2. Statement A1 is selected and, in response, statement A2 is also highlighted or otherwise indicated.

In response to the selection of the selected statement 304 from the source vocabulary, a second region 306 lists mapped statements from the target vocabulary 112 mapped from the selected statement 304. In some embodiments, the listed statements in the second region 306 are ordered by similarity scores 308. A second statement 310 is selected from the list of mapped statements. A confirmation indicator 312, such as a button, indicates that the selected statement 304 and the second statement 310 are confirmed as mapped. A message 314 confirms that the mapping is added to the confirmed mappings database 166.

Indicators of Boolean operators 316 on the display 300 provide the ability to create or modify the rules governing the use of the second statement 310. For example, A1 maps to B1 and A2 maps to B2. The indicators of Boolean operators 316 can be used to indicate that B1 and B2 are mutually exclusive. In some embodiments, the indicators of the Boolean operators 316 can be omitted.

The mapping interface 160 can be used to operate the system 100 interactively. Selected general concepts can be indicated for determining mappings. Selected features or keywords can be indicated for determining mappings. The selected general concepts and/or selected features are used as the basis for determining the matches or mappings between the selected statement 304 in the source vocabulary 110 and the list of statements mapped from the target vocabulary 112. The computed similarity score 308 can be computed according to the selected generalized concept(s) and/or feature(s).

In the illustrated example, an indicator for generalized concept of the anatomical structure 318 and an indicator for the generalized concept of the foreign object 320 are selected or turned on. In response to the selected anatomical structure indicator 318, the extracted feature or words "tricuspid valve" is underlined in the selected statement 304.

In response to the selected foreign object indicator 320, the extracted feature or words "prosthetic" is underlined in the selected statement 304. The list of mapped statements 310 are determined based on matching between anatomical structure and foreign object. The similarity scores 308 are computed based on the similarity of the anatomical structure and the foreign object. In each of the mapped statements 310 from the target vocabulary 112, the extracted features of the matching identified concept of "tricuspid valve" and/or matching identified concept of "prosthesis" are underlined.

In some instances, the ability to selectively turn on and off selected general concepts provides a mechanism for a flexible mapping environment. In some instances, the healthcare practitioner can operate the interface from the most stringent criteria of all generalized concepts selected to more open consideration of intent in the mappings with fewer generalized concepts selected. In some instances, this can aid the healthcare practitioner in working with mappings of large numbers of finding codes.

Figure 4:
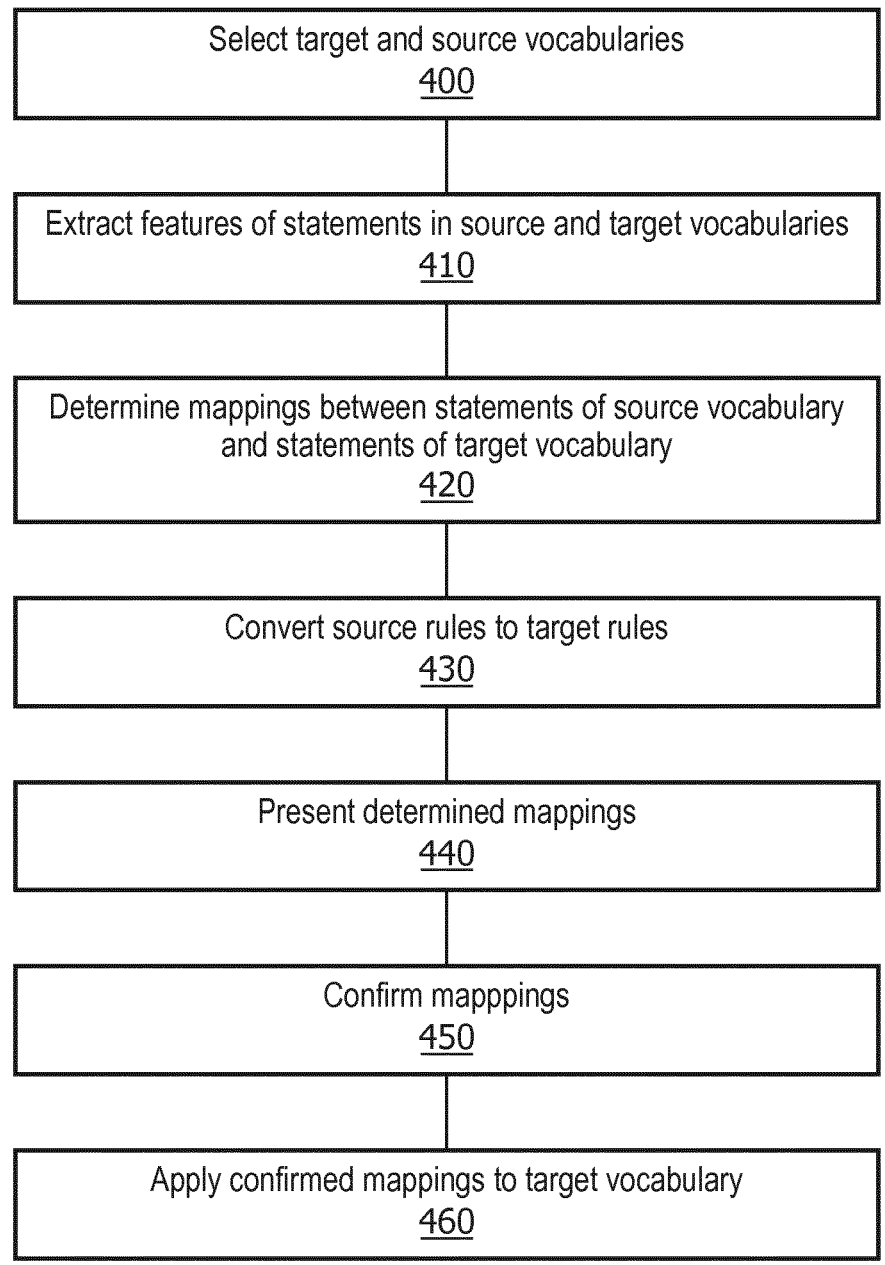
FIG. 4 illustrates a flowchart in accordance with an embodiment(s) herein.

FIG. 4 illustrates a flowchart in accordance with an embodiment(s) herein.

At 400, the source vocabulary 110 and the target vocabulary 112 are selected. Each of the vocabularies 110, 112 includes unique finding codes and corresponding statements. Each of the vocabularies 110, 112 can include rules that govern the use of the finding codes in preparing a patient's medical report. Each of the vocabularies 110, 112 can include statistical information about the use of the finding codes in prior medical documents.

At 410, features of the corresponding statements of each vocabulary 110, 112 are extracted using NLP techniques. The NLP techniques include word tokenization and stemming, phrase identification, and stop word elimination. Concepts are identified from extracted words or phrases. The identified concepts are generalized using an ontology. The generalized concepts include a foreign object, an anatomical structure, a finding, a severity indicator, a pathology, an image quality indicator, a polarity, a certainty indicator, and combinations thereof.

At 420, the extracted features between statements in the source vocabulary 110 and statements in the target vocabulary 112 are compared using the generalized concepts and identified concepts, and mappings are determined. The comparison can include different combinations of the generalized concepts. The mappings can be represented with a link between one statement in the source vocabulary 110 and one statement in the target vocabulary 112. The mappings include computation of one or more similarity scores. The computation of a similarity score can include an overall comparison between the compared statements, such as word overlap, statistical information, and the like.

At 430, rules that govern the use of the source vocabulary 110 can be converted to rules that govern the use of the target vocabulary 112 according to the determined mappings. The rules can include conditional usage, such as If-Then logic. The rules can include Boolean operators. In some embodiments, act 430 can be omitted.

At 440, the determined mappings are visually presented. The determined mappings can be presented on the display device 162. The presented mappings can include one or more similarity scores for each mapped statement in the target vocabulary 112. The determined mappings can be represented as a selected statement in the source vocabulary 110 and a list of mapped statements in the target vocabulary 112. The list of mapped statements in the target vocabulary 112 can be ordered by similarity score.

At 450, confirmed mappings are indicated in response to an input from the input device 164. Confirmed mappings can be stored in the database of confirmed mappings 166.

At 460, the confirmed mappings are applied to the target vocabulary 112. That is, statements are added or modified in the target vocabulary 112 according to the confirmed mappings.

The above may be implemented by way of computer readable instructions, encoded or embedded on a computer readable storage medium, which, when executed by a computer processor(s), cause the processor(s) to carry out the described acts. Additionally or alternatively, at least one of the computer readable instructions is carried out by a signal, carrier wave or other transitory medium.

The above steps can be performed in a different order and/or some steps can be omitted.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with, or as part of other hardware, but may also be distributed in other forms, such as via the Internet or other wired or wireless telecommunication systems. Any reference signs in the claims should not be construed as limiting the scope.

The invention claimed is:

1. A method, comprising:
   extracting first features of a first statement of a first finding code in a source vocabulary, wherein the first features are words of the first statement;
   extracting second features of a second statement of a second finding code in a target vocabulary, wherein the second features are words of the second statement, wherein the source vocabulary and the target vocabulary include different vocabularies for a same observational or diagnostic statement;
   identifying a concept from each of the extracted first and second features;
   generalizing the identified concepts to determine generalized concepts;
   defining a set of possible results to include 1) first and second features include a same generalized concept and the first and second features include a same feature, 2) the first and second features include the same generalized concept and the first and second features do not include the same feature, 3) the first feature includes the generalized concept and the second feature does not include the generalized concept or the second feature includes the generalized concept and the first feature does not include the generalized concept, and 4) the first and second features do not include the same generalized concept;
   determining a mapping between the first statement of the source vocabulary and the second statement of the target vocabulary by comparing the extracted first and second features based on a generalized concept for at least one concept identified from the extracted first and second features to match the extracted first and second features, wherein a result of the mapping is from the set of possible results;

computing a similarity score between the first statement of the source vocabulary and the second statement of the target vocabulary based on the result of the mapping and a point system that adds points to the similarity score or subtracts points from the similarity score;

presenting the first statement on a display device; and presenting the second statement with the similarity score on the display device.

2. The method according to claim 1, further comprising:
filtering, prior to extracting the first and second features, at least one of the source vocabulary and the target vocabulary according to statistical information to exclude finding codes failing to satisfy a predetermined threshold.

3. The method according to claim 1, further including:
converting a set of rules for the first finding code in the source vocabulary to a set of rules for the second finding code in the target vocabulary according to the determined mapping.

4. The method according to claim 1, wherein the mapping includes a word overlap ratio computed between words or phrases of the compared extracted first and second features.

5. The method according to claim 4, further including:
computing the word overlap ratio as a number of unique words or phrases that are in common among the extracted first and second features divided by a number of unique words or phrases in either the extracted first or second features.

6. The method according to claim 1, wherein the first statement of the source vocabulary and the second statement of the target vocabulary comprise codified medical statements.

7. The method according to claim 1, further including:
confirming the determined mapping between the first statement of the source vocabulary and the second statement of the target vocabulary in response to an input from an input device.

8. The method according to claim 7, further comprising:
applying the confirmed mapping to the target vocabulary, which modifies the second statement.

9. The method according to claim 8, further comprising:
displaying a message indicating the mapping has been applied to the target vocabulary to modify the second statement.

10. The method according to claim 1, wherein the point system assigns a different value for each outcome in the group of the possible outcomes of the result.

11. The method according to claim 10, wherein the point system adds, to the similarity score:
a first predetermined value in response to the first and second features including the generalized concept and the same feature;
a second predetermined value in response to the first and second features including the generalized concept and not including the same feature;
a third predetermined value in response to the first features including the generalized concept and the second features not including the generalized concept or the second features including the generalized concept and the first features not including the generalized concept; and
a fourth predetermined value in response to the first and second features not including the generalized concept.

12. The method according to claim 1, further comprising:
computing the similarity score based on a statistical model.

13. The method according to claim 1, further comprising:
computing the similarity score based on a machine learning model.

14. The method according to claim 1, further comprising:
computing the similarity score based on a prior mapping of another vocabulary.

15. The method according to claim 1, wherein the generalized concepts comprise at least one selected from a group comprising of a foreign object, an anatomic structure, a finding, a severity indicator, a pathology, an image quality indicator, a polarity, and a certainty indicator.

16. The method according to claim 1, further comprising:
receiving a user input to create or modify a rule governing use of the second statement.

17. The method according to claim 16, wherein the input indicates a user selected Boolean operator from a set of user selectable Boolean operators.

18. The method according to claim 1, further comprising:
extracting features of a statement of at least one other finding code in the target vocabulary;
determining mappings between the first statement and the statement of the at least one other finding code by comparing the extracted first features and the extracted features based on the generalized concept to match the first statement and the statement of at least one other finding code,
computing a similarity score between the first statement and the statement of at least one other finding code based on the result of the comparing;
presenting the first statement on a display device; and
presenting the statement of the at least one other finding code with the corresponding similarity score on the display device.

19. A method, comprising:
a feature extraction engine configured to:
extract first features of a first statement of a first finding code in a source vocabulary;
extract second features of a second statement of a second finding code in a target vocabulary,
wherein the source vocabulary and the target vocabulary include different vocabularies for a same observational or diagnostic statement;
identify at least one concept from the extracted first and second features; and
generalize the identified concept to determine a generalized concept; a finding code comparison engine configured to:
determine a mapping between the first statement of the source vocabulary and the second statement of the target vocabulary by comparing the extracted first and second features based on the generalized concept for the at least one concept identified from the extracted first and second features to match the extracted first and second features,
wherein a result of the mapping is from individual comparisons from a predetermined group of possible outcomes that, include: the first and second features include the generalized concept and the first and second features include a same feature, the first and second features include the generalized concept and the first and second features do not include the same feature, the first features include the generalized concept and the second features do not include the generalized concept or the second features include the generalized concept and the first features do not include the generalized concept, and the first and second features do not include the generalized concept; and compute a similarity score between the first statement of the source vocabulary and the second statement of the target vocabulary based on the result of the mapping and a point system;

a mapping interface configured to present the first statement on a display device and present the second statement with the similarity score on the display device.

20. A non-transitory computer-readable storage medium carrying instructions which controls one or more processors to:

extract first features of a first statement of a first finding code in a source vocabulary;

extract second features of a second statement of a second finding code in a target vocabulary, wherein the source vocabulary and the target vocabulary include different vocabularies for a same observational or diagnostic statement;

identify at least one concept from the extracted first and second features; and generalize the identified concept to determine a generalized concept;

determine a mapping between the first statement of the source vocabulary and the second statement of the target vocabulary by comparing the extracted first and second features based on the generalized concept for the at least one concept identified from the extracted first and second features to match the extracted first and second features, wherein the mapping is determined from individual comparisons of each of:

the first and second features include the generalized concept and the first and second features include a same feature, the first and second features include the generalized concept and the first and second features do not include the same feature, the first features include the generalized concept and the second features do not include the generalized concept or the second features include the generalized concept and the first features do not include the generalized concept, and the first and second features do not include the generalized concept; compute a similarity score between the first statement of the source vocabulary and the second statement of the target vocabulary based on the result of the mapping and a point system;

present the first statement on a display device; and present the second statement with the similarity score on the display device.

* * * * *